United States Patent [19]

Grendahl

[11] Patent Number: 4,778,462

[45] Date of Patent: Oct. 18, 1988

[54] MULTIPLE ELEMENT ZONE OF FOCUS ARTIFICIAL LENS

[76] Inventor: Dennis T. Grendahl, 2070 Shoreline Dr., Orono, Minn.

[21] Appl. No.: 88,412

[22] Filed: Aug. 24, 1987

[51] Int. Cl.$^4$ ............................................. A61F 2/16
[52] U.S. Cl. ......................................... 623/6; 623/5;
351/161; 351/168
[58] Field of Search .................. 623/6; 351/161, 162, 351/168, 171

[56] References Cited

U.S. PATENT DOCUMENTS

| | | | |
|---|---|---|---|
| 4,450,593 | 5/1985 | Poler | 623/6 |
| 4,655,565 | 4/1987 | Freeman | 623/6 |
| 4,666,446 | 5/1987 | Noziol | 623/6 |
| 4,704,016 | 11/1987 | de Carle | 351/161 |

FOREIGN PATENT DOCUMENTS

| | | | |
|---|---|---|---|
| 0162573 | 11/1985 | European Pat. Off. | 623/6 |
| 8603961 | 7/1986 | PCT Int'l Appl. | 623/6 |
| 2181355 | 4/1987 | United Kingdom | 623/6 |

Primary Examiner—Richard J. Apley
Assistant Examiner—James Prizant
Attorney, Agent, or Firm—Hugh D. Jaeger

[57] ABSTRACT

An implantable or contact lens for replacement of a defective natural lens in an eye in which various portions of the lens have different powers and focal lengths to produce in-focus images on different portions of the retina, of objects which are located at various distances from the eye, thereby substituting for the natural focusing action of the eye. The image processing capability of the brain functions to largely ignore the out-of-focus images and concentrate on the in-focus image of the object selected by the brain for consideration.

11 Claims, 13 Drawing Sheets

MULTIPLE ELEMENT ZONE OF FOCUS ARTIFICIAL LENS

CROSS REFERENCES TO CO-PENDING APPLICATIONS

This application is related to Application Ser. No. 07/088,428, filed Aug. 24, 1987, "Laminated Zone of Focus Artificial Lens"; Application Ser. No. 07/088,413, filed Aug. 24, 1987, "Cylindrically Segmented Zone of Focus Artificial Lens"; and Application Ser. No. 07/088,249, filed Aug. 24, 1987, "Radially Segmented Zone of Focus Artificial Lens".

BACKGROUND OF THE INVENTION

1. Field of the Invention

The present invention pertains to an implantable intraocular lens, and more particularly, pertains to a lens containing multiple lens elements.

This invention relates to lenses which have areas which serve to bring impinging rays to a focus in specific areas of the focal plane. Such lenses are called zone of focus lenses and are particularly useful for implantation into the eye as a substitute for the natural lens since, in combination with the brain, they effectively replicate the ability of the natural lens to bring objects at varying distances to a sharp focus.

The invention relates specifically to a zone of focus lens in which the lens is made up of discrete lens elements distributed over the surface of the lens. Each element serves to bring the impinging rays from an object at a predetermined distance to a focus on a particular region of the retina. By selecting various powers for the elements, it is possible to have an object at a given distance brought to an acceptable focus by at least one of such elements. In this manner, an in-focus image (sharp image) is created on a particular portion of the retina serviced by that element. It has been found that the processing of the image by the brain results in the selective consideration of the sharpest image and the virtual discard of the other out-of-focus images created by other elements.

2. Description of the Prior Art

Limited attempts have been made to produce a lens having areas of varying powers. There have been many attempts to produce implantable lenses which serve for both close and far seeing, similar to the bifocal spectacles. In general, such lenses have been produced with two regions having different powers. The light which impinges on the retina passes through one region to the exclusion of the other. In such a system, only one region of the lens is used at a time, and there is no accommodation by the brain to reject an out-of-focus image. Great care and accuracy must be used in the preoperative measurements since both the near and far powers must be accurately determined. Since the near and far powers are not specifically interrelated, the inventory requirements are compounded since a variety of near powers must be available for every far power.

SUMMARY OF THE INVENTION

The lens is a composite of individual lens elements, each of which has a distinct power and focal length. Each element brings the impinging rays to bear on a predetermined portion of the retina, which may be either unique to that element or shared with other elements of like power. The elements are selected to have a sufficient range of powers to accommodate the projected use. That is, the value of the power and the number of elements will be determined by the projected use. Most uses can be accommodated with a lens having two or three powers to accommodate objects at near, far and intermediate distances. These powers can be distributed among a like number of elements or a number of elements which is two, three or even more times the number of powers. The distribution of powers among the elements need not be done equally. For example, if most of the sight is required at close distances, the number of elements for this distance can be increased and the number of elements for far vision correspondingly decreased.

Accommodation of the brain to such an arrangement may be enhanced by adding a distinctive color to the elements of like power. This approach may be utilized where loss or impairment of color vision is of little consequence.

Elements of differing powers can be provided by molding, grinding, lathe cutting or otherwise forming individual lens elements from materials having different indices of refraction and mounting them in an assembly to form a unitary lens structure.

In the alternative, the individual lens elements can be fabricated of like material and the differing powers obtained by grinding, molding or otherwise shaping the surface of the individual lens elements to provide individual curvatures.

Lens is a generic term for intraocular lens, intracorneal lens, or contact lens.

It is a principal object hereof to provide a lens incorporating a multiple element zone of focus.

It is therefore an object of this invention to provide a zone of focus lens which will make the replacement of a defective natural lens available to many who cannot now afford the operation.

It is another object of the invention to provide a zone of focus lens which does not require either an extensive inventory of various powers and combination of powers or extensive preoperative measurement prior to implantation into the eye as a replacement for a defective lens.

Still another object of this invention is to provide an approach to the replacement of a defective lens by providing a very nearly universal lens which provides vision adequate to allow a normal life style.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE INVENTION

Figure 1:
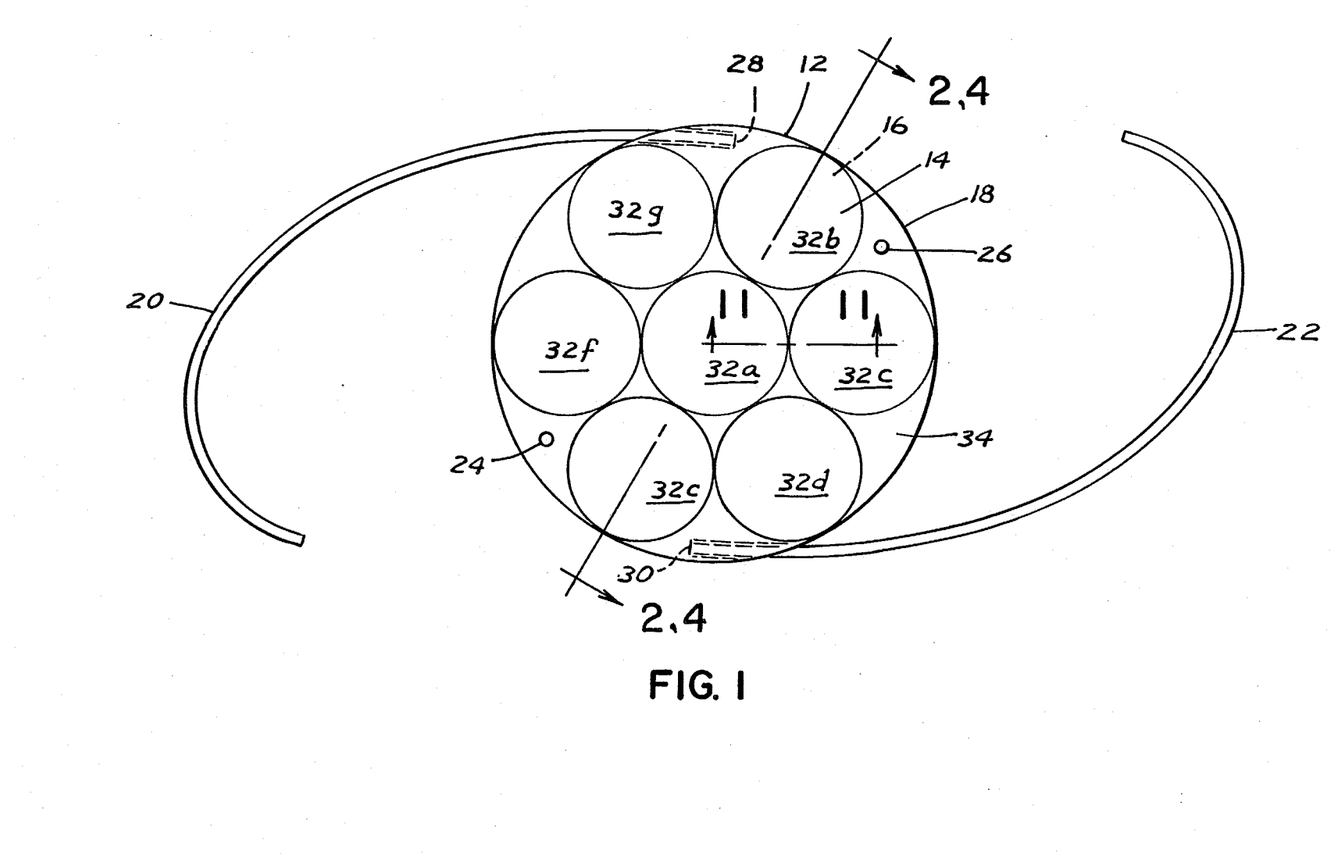
FIG. 1 illustrates a plan view of a multiple element zone of focus lens according to the invention.

FIG. 1 illustrates a plan view of a multiple element zone of focus implantable lens 10, of PMMA or other suitable material, which includes an optic 12, a convex anterior surface 14, a posterior surface 16, an edge 18 therebetween, open loop haptics 20 and 22 for fixation of the lens to the interior of the eye and positioning holes 24 and 26. Haptics 20 and 22 secure into holes 24, 28 and 30 by known processes. The shape of lens 10 may be varied to accommodate optical or other requirements. The lens 10 is primarily illustrated as a plano convex lens, but can assume any other convenient shape, such as meniscus, biconvex, or any other desired lens shape. Lens 10 has a plurality of lens elements 32a–32g contained in the lens body 34. Each of the elements 32a–32g have a distinct focal length or power so as to bring objects of differing distance into focus in a common focal plane. In general, it will be found that two or three powers will be optimum in terms of performance within the human eye. Fewer powers will not provide adequate sharp images for consideration by the brain, and may unduly complicate the process of adaption by the patient. With two different powers, the lenses of like power can be positioned to be interspersed with lenses of the other power. Alternatively, lenses of like power may be located in the regions where adaptation is facilitated. Further alternatives include locating the lenses in accordance with physical characteristics of the eye itself to accommodate retinal or corneal defects. While seven lens elements are shown in the embodiment of FIG. 1, it will be appreciated that the invention is not so limited, and either a greater or smaller number of lens elements is permissible. The power of the individual lens elements 32a–32g is determined by their radius of curvature and the index of refraction, either of which may be varied to provide the desired power. In the embodiment of FIG. 1, the radius of curvature for lens elements 32a–32g are the same and the index of refraction of the material is varied to provide the necessary difference in power. In the case where it is desired to make lens 10 of PMMA, the index of refraction can be modified by changing the length of the polymer while maintaining compatibility with the other characteristics, or by the introduction of suitable additives. Alternatively, some of the lens elements can be made from PMMA and others from polycarbonate. If glass is to be used, it is possible to select glass according to the desired index of refraction. Fabrication of the lens 10 may begin with the creation of a composite rod or similar structure in which the cross-section of the rod resembles the plan view of FIG. 1. Such a rod can be made by simultaneous extrusion of the lens elements from differing material or by individual extrusion or other shaping and subsequent joining of the lens elements. While the extrusion process has certain advantages, particularly that of low cost, the individual fabrication of the lens elements and subsequent joining affords the opportunity to mask the junction with an anti-reflective coating. In either case, the resulting blank may be sliced and fabricated into lenses either by further molding in a die which has the radii of curvature for the desired optical characteristics, by conventional lathe cutting, or other similar optical finishing techniques.

Figure 2:
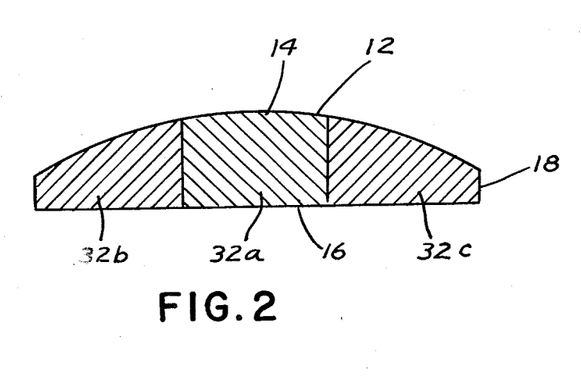
FIG. 2 illustrates a cross-section of the multiple element zone of focus lens taken along line 2—2 of FIG. 1.

FIG. 2 illustrates a cross-sectional view taken along line 2—2 of FIG. 1 where all numerals correspond to those elements previously described.

Figure 3A:
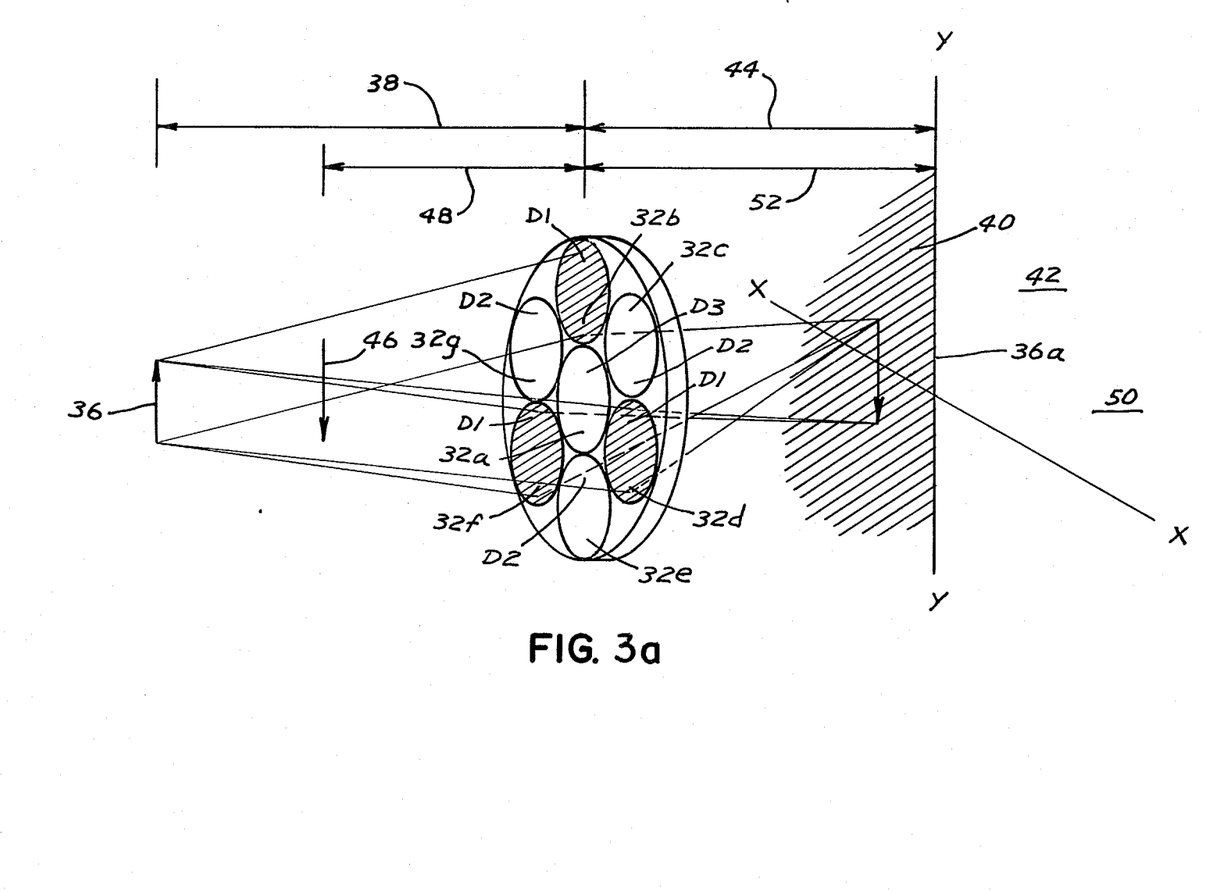
FIGS. 3A and 3B illustrates a schematic isometric view of an optical system in which the zone of focus lens develops images for each like lens element.
Figure 3B:
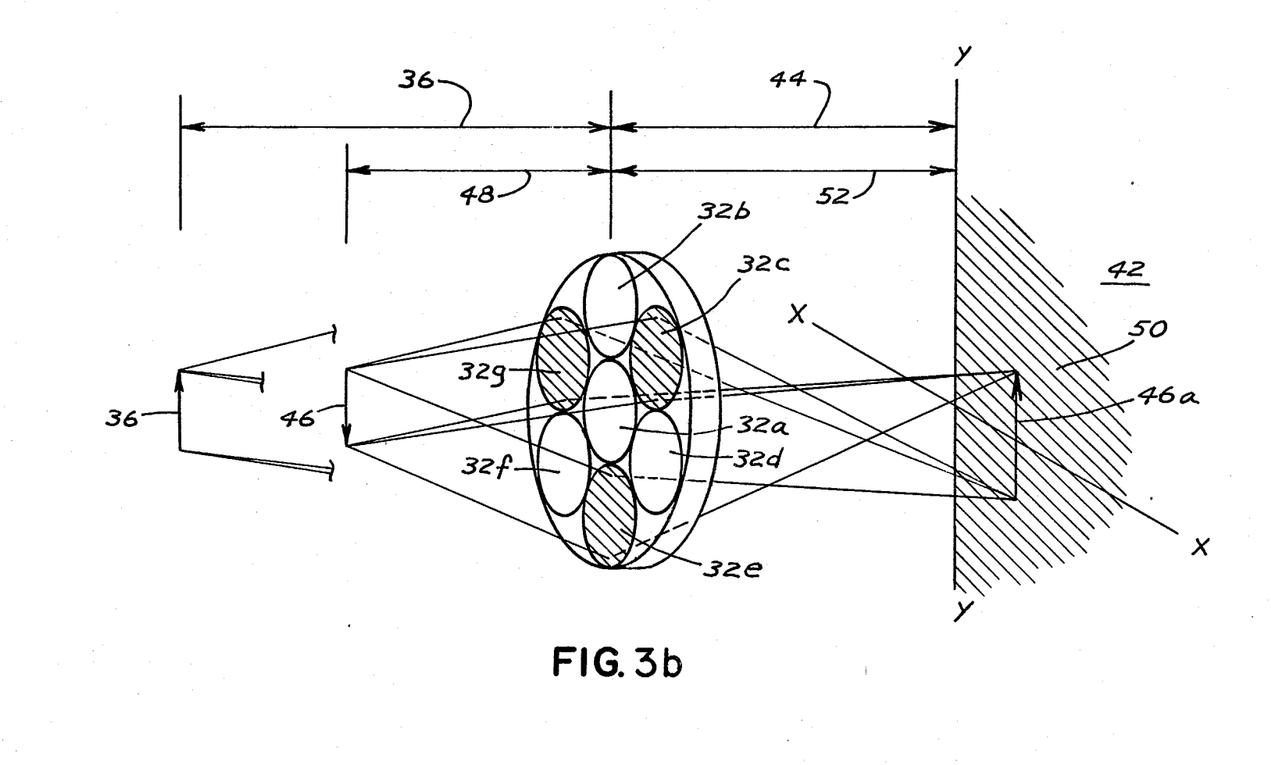

FIGS. 3A and 3B are schematic illustrations of an optical system utilizing the lens of FIG. 1 which incorporates two illustrations for the purpose of clarity, and where all numerals correspond to those elements previously described. The lens 10 has a plurality of lens elements 32a–32g. The lens elements 32b, 32d and 32f have a common power D1 and bring a far object 36 located at a far distance 38 to focus on a focal area 40, and is shown as image 36a, which lies on retinal focal plane 42 as indicated by an x-y axis at a far focal distance 44, which terminates at the retinal focal plane 42. In FIG. 3 the elements 32c, 32e and 32g have a common power D2 and bring a near object 46, located at a near distance 48 to a focus in focal area 50 at a near focal distance 52 also terminating at the retinal focal plane 42. The lens element 32a can have a third power D3 or can have a power D1 or D2. It can be seen that the lens elements 32b, 32d and 32f of lens 10 each produce an image 36a in the focal plane on a focal area 40. Similarly, elements 32c, 32e and 32g produce an image 46a on a common focal area 50 which is separate and distinct from the focal area 40. Lens element 32a may have a unique power and develop an image in a unique third area, not shown for sake of clarity and brevity, or may have a power and optical orientation to produce a sharp image of far object 36 in the focal area 40 of the retinal focal plane 42, or a power and optical orientation to produce a sharp image of near object 46 in the focal area 50 of the retinal focal plane 42.

It will be appreciated that the lens elements 32b, 32d and 32f, in addition to producing a sharp image of far object 36, will also produce an out-of-focus image of near object 46. Similarly, the lens elements 32c, 32e and 32f will simultaneously produce a sharp image of near object 46 and an out-of-focus image of far object 36. The adaptive power of the brain effectively rejects the out-of-focus image and permits the in-focus image of the desired object to predominate. The adaptive capability varies with individuals and can sometimes be enhanced by selective positioning of the segments in accordance with personal characteristics of the individual.

Figure 4:
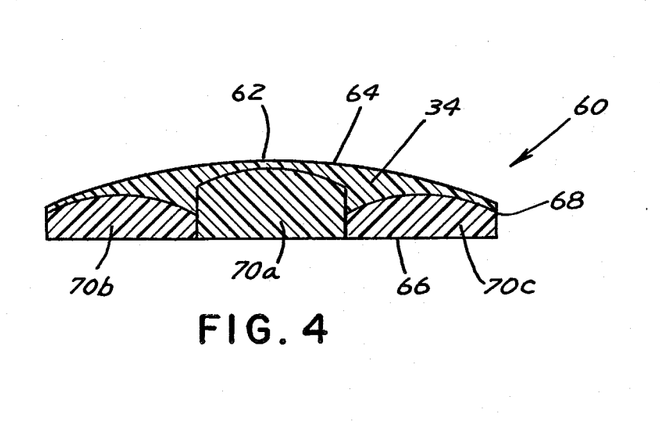
FIG. 4 illustrates a cross-sectional view of an embodiment in which the lens elements of the segmented zone of focus lens are round taken along line 4—4 of FIG. 1.

FIG. 4 illustrates a cross-sectional embodiment of a lens 60 including an optic 62 which includes a convex anterior surface 64, a planar posterior surface 66, an edge 68 therebetween, and a plurality of lens elements 70a–70g where the lens elements 70a–70g are round and affix within a lens body 72 with a suitable adhesive or other material for molding them as an integral part of lens body 72. The plan view of the lens 60 is the same as for the lens 10 in FIG. 1 where the plurality of lens elements 32a–32g correspond in overhead plan view to the corresponding lens elements of this FIG. in which the alphabetic letters correspond such as 70a being equivalent to 32a and so forth. The differing powers are provided by fabricating the lens elements with different radii of curvature. Since the segments do not have a uniform curvature, conventional grind or lathe cutting techniques are not generally adequate for fabrication where the lens elements are an integral assembly with the lens body 72. Where the integral structure is desired, it may be desirable to form the lens in a die having suitable dimensions or, as previously described, individually fabricate the lens elements and join them after the curved surface is fabricated.

Figure 5:
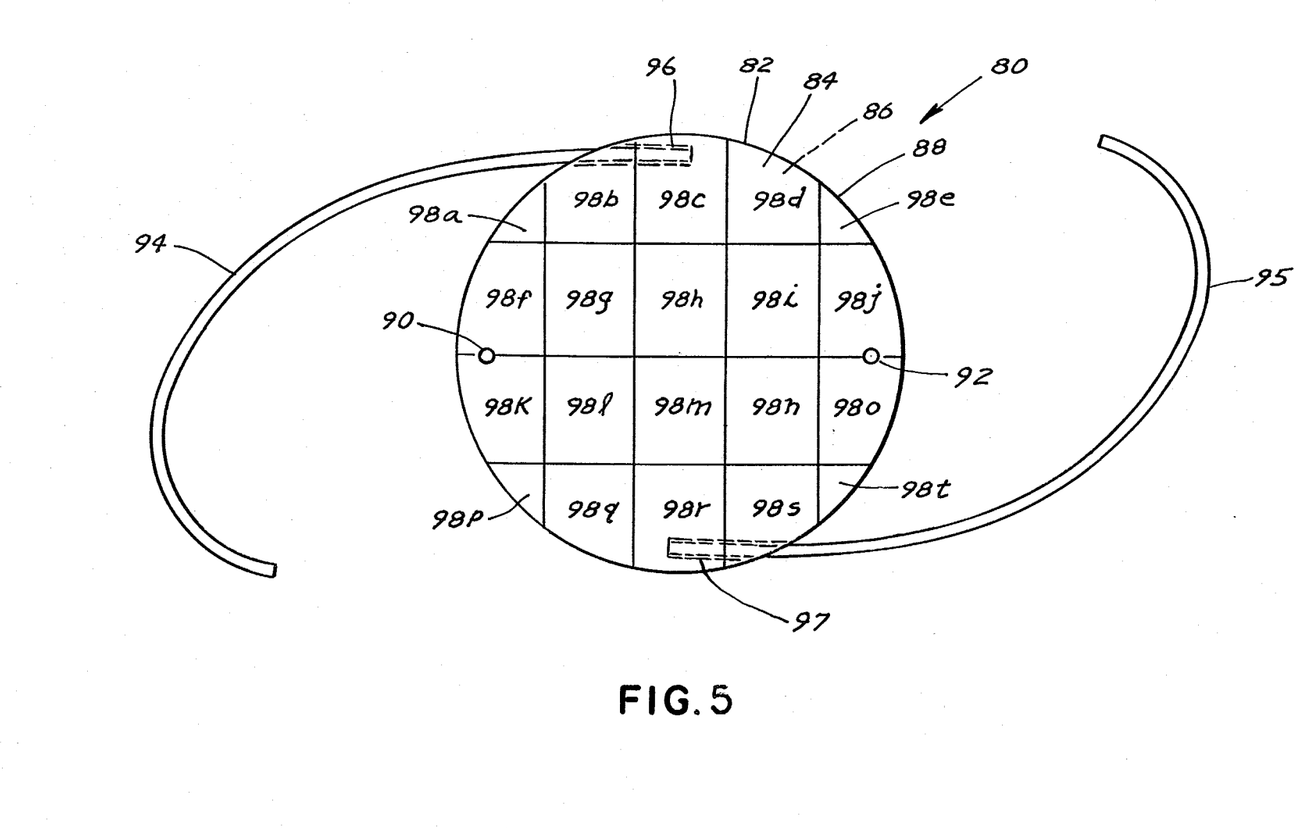
FIG. 5 illustrates a plan view of an embodiment of the multiple element zone of focus lens having rectangular lens elements.

FIG. 5 illustrates an embodiment of the zone of a focus lens 80, including an optic 82, in which the lens elements 98a–98u are generally rectangular in shape and having a uniform radius of curvature, including a convex anterior top surface 84, a plano posterior surface 86, an edge 88 therebetween, and positioning holes 90–92 and haptics 94–95 engaged in holes 96–97. A structure such as this can be fabricated by extrusion, using compatible plastic materials which have different indices of refraction. Alternatively, a composite structure can be made by assembling rectangular rods, having different indices of refraction, into a unitary assembly and slicing blanks therefrom. The blanks can be processed into lenses with conventional techniques. The rods can be affixed to each other with suitable adhesive.

In addition to having different indices of refraction, the individual elements can be made of different colors. The individual lens elements 98a, 98c, 98e, 98g, 98i, 98k, 98m, 98o, 98q and 98s have like powers; bring incident rays to focus on a common area; and are colored red or some other suitable color. Lens elements 98b, 98d, 98f, 98h, 98j, 98l, 98n, 98p, 98r and 98t have like powers, differing from the common power of the other group of elements; bring incident rays to a focus on a common area distinct from the area of the other group of elements; and are of a different suitable color such as blue. Thus, colors are assigned to specific lens powers to assist the brain in distinguishing the images produced from the two groups of elements.

Figure 6:
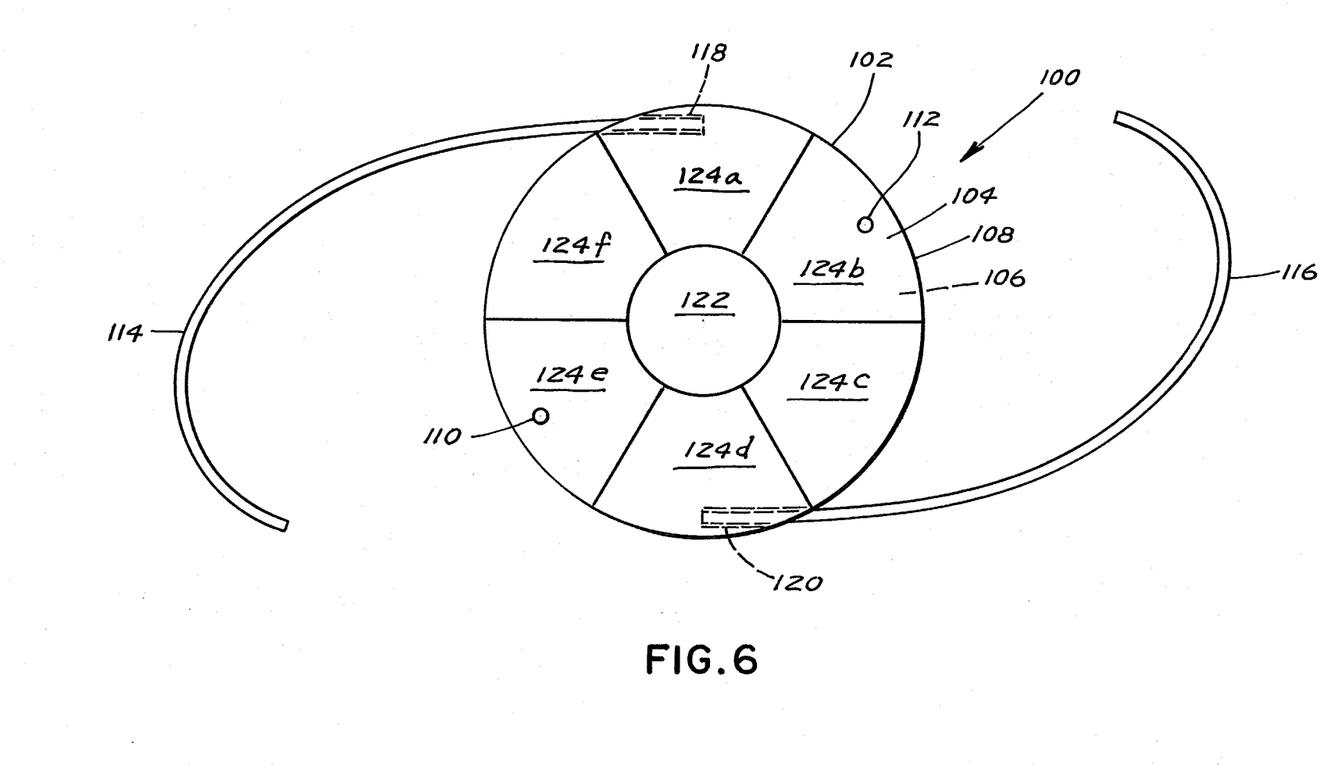
FIG. 6 illustrates a plan view of an embodiment of the multiple element zone of focus lens having a combination of round and pie-shaped lens elements.

FIG. 6 illustrates an embodiment of a lens 100, including an optic 102, a convex anterior surface 104, a plan surface 106, an edge 108 therebetween, and positioning holes 110 and 112 and haptics 114 and 116 engaged in holes 118 and 120. An optic 102 includes a cylindrical central lens element 122 and a plurality of peripherally located radial lens elements 124a–124f about the central lens element 122. The lens elements 122 and 124a–124f may be various powers and colors having the lens elements with common powers of the same color. The lens elements with common powers are optically aligned to produce an image on a common area of the retina.

Figure 7:
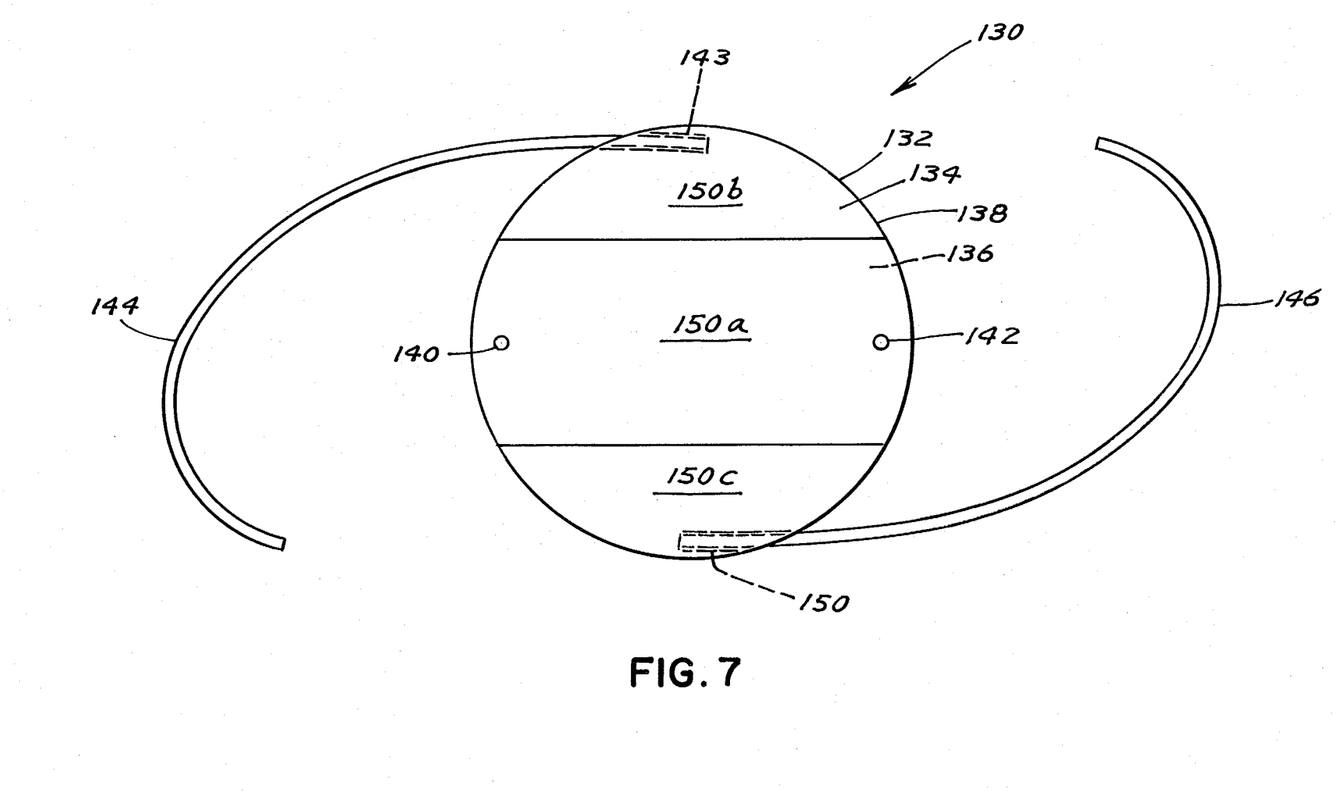
FIG. 7 illustrates a plan view of an embodiment of the multiple element zone of focus lens having horizontal divisions between the lens elements.

FIG. 7 illustrates an embodiment of a lens 130 including an optic 132, a convex anterior surface 134, a plano surface 136, edge 138 therebetween, and positioning holes 140–142 and haptics 144–146 engaged in holes 148–150. The lens optic 132 is made up of lens elements 150a–150c which are joined along the corresponding horizontal axis between the lens elements 150a–150c. In the case where three different powers are used for the three lens elements 150a–150c, the elements may be optically aligned to produce an image on the retina in the area corresponding roughly to the geometry of the lens 130. The haptics 144 and 146 will be located to provide the optimum ease of adaptation. For some persons, the optimum position for the most commonly used image brought to a focus by lens element 150a, will be the horizontal central portion of the retina. If this is the case, the haptics 144 and 146 will be located to place lens element 150a in a position to bring its image to the central portion of the retina.

Figure 8:
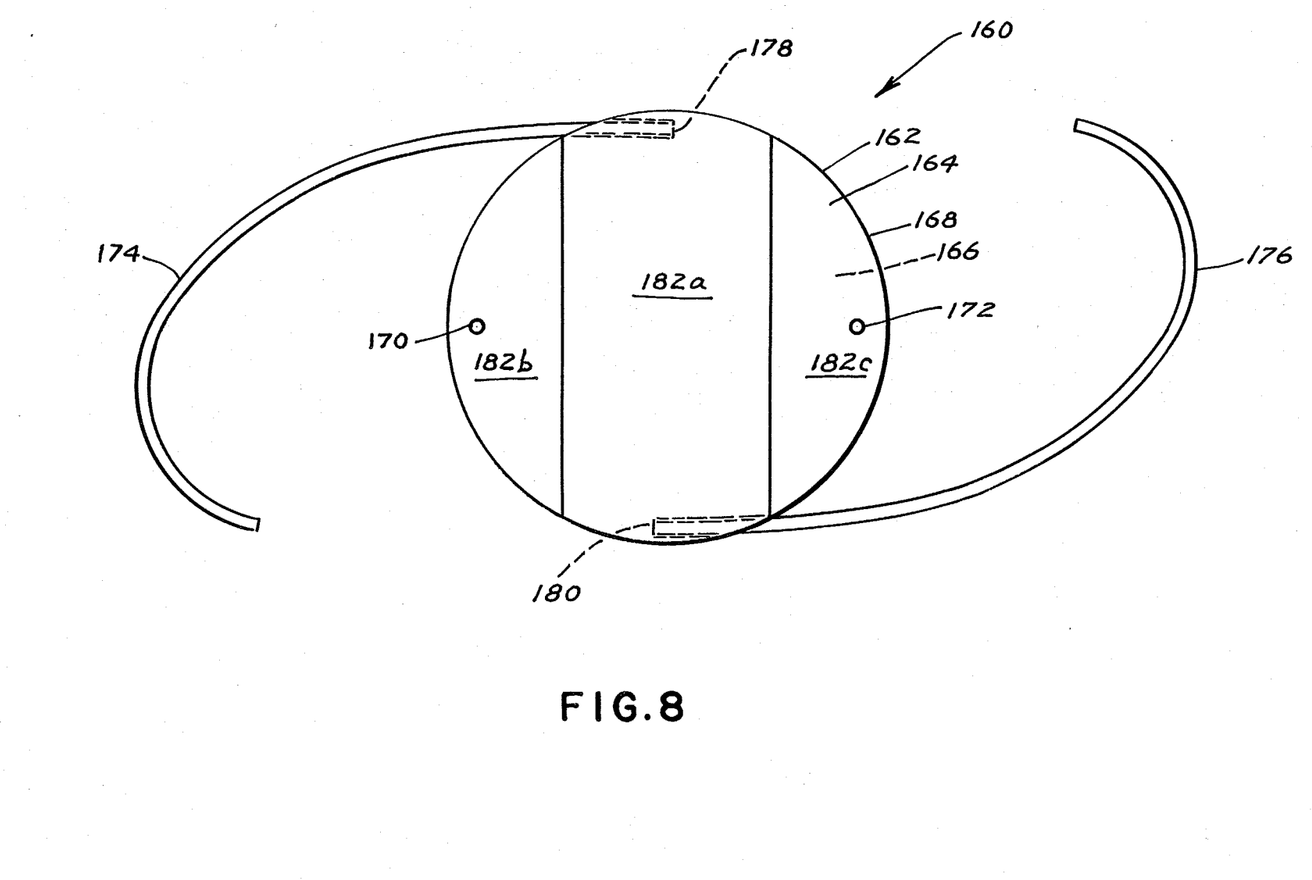
FIG. 8 illustrates a plan view of an embodiment of the multiple element zone of focus lens having vertical divisions between the lens elements.

FIG. 8 illustrates a three-element embodiment of a lens 160 similar to that of FIG. 7 with the haptics arranged to place the central element in the vertical orientation. The lens 160 includes an optic 162, convex anterior surface 164, posterior surface 166, an edge 168 therebetween, and positioning holes 170–172 and haptics 174 and 176 engaged in holes 178 and 180. The optic 162 includes lens elements 182a–182c joined along the corresponding axis between the lens elements 182a–182c. The lens elements of FIGS. 7 and 8 can be colored blue, red or yellow or be transparent. The lens elements can be of the same or different powers, but it is desirable that like powers share a common area of the retina.

Figure 9:
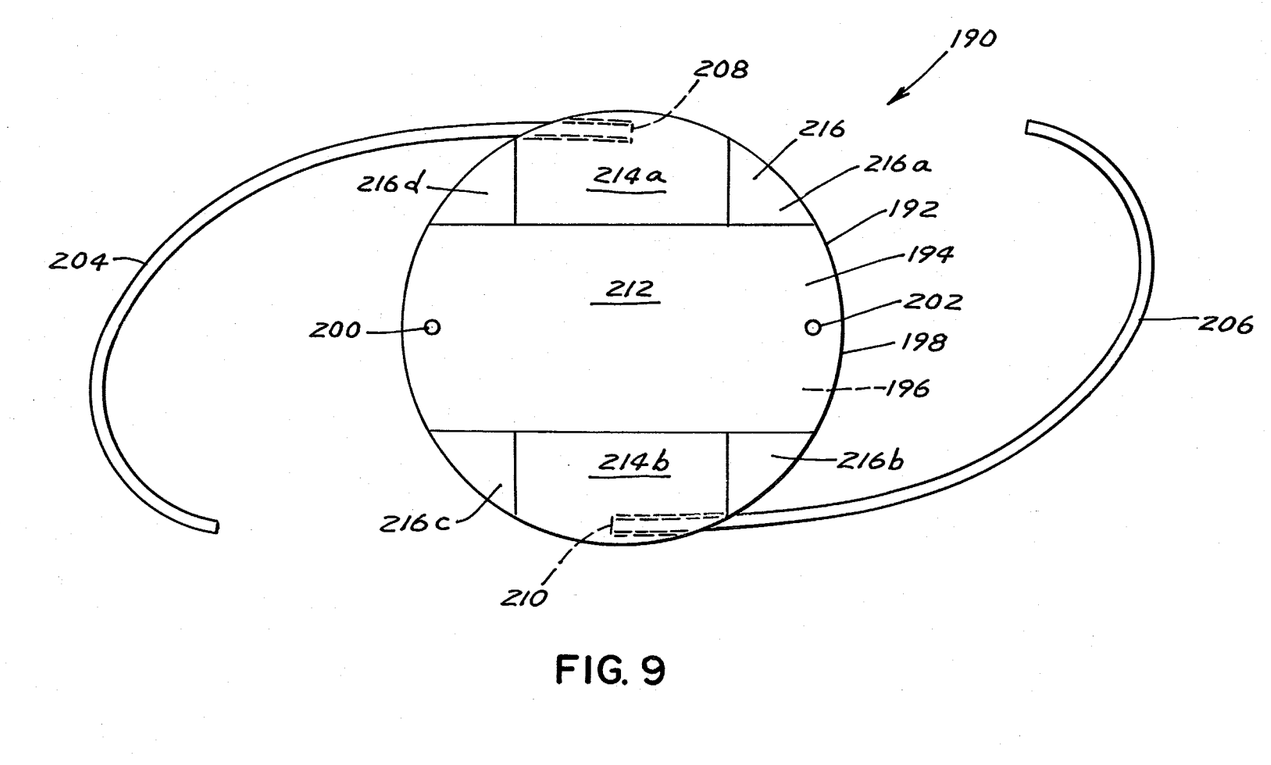
FIG. 9 illustrates a plan view of an embodiment of the multiple element zone of focus lens having both horizontal and vertical divisions between the lens elements with the horizontal lens element dominating.

FIG. 9 illustrates a geometric arrangement in which the horizontal central element has substantially more area than the other elements. The lens 190 includes an optic 192, a convex anterior surface 194, a plano posterior surface 196, an edge 198 therebetween, and positioning holes 200 and 202 and haptics 204 and 206 engaged in holes 208 and 210. The optic 192 includes a horizontally aligned lens element 212, vertically aligned lens element portions 214a and 214b perpendicular to the horizontally aligned lens element 212 in a lens body 216 including portions 216a–216d. This geometrical configuration may employ combinations of differing powers and colors as previously described.

Figure 10:
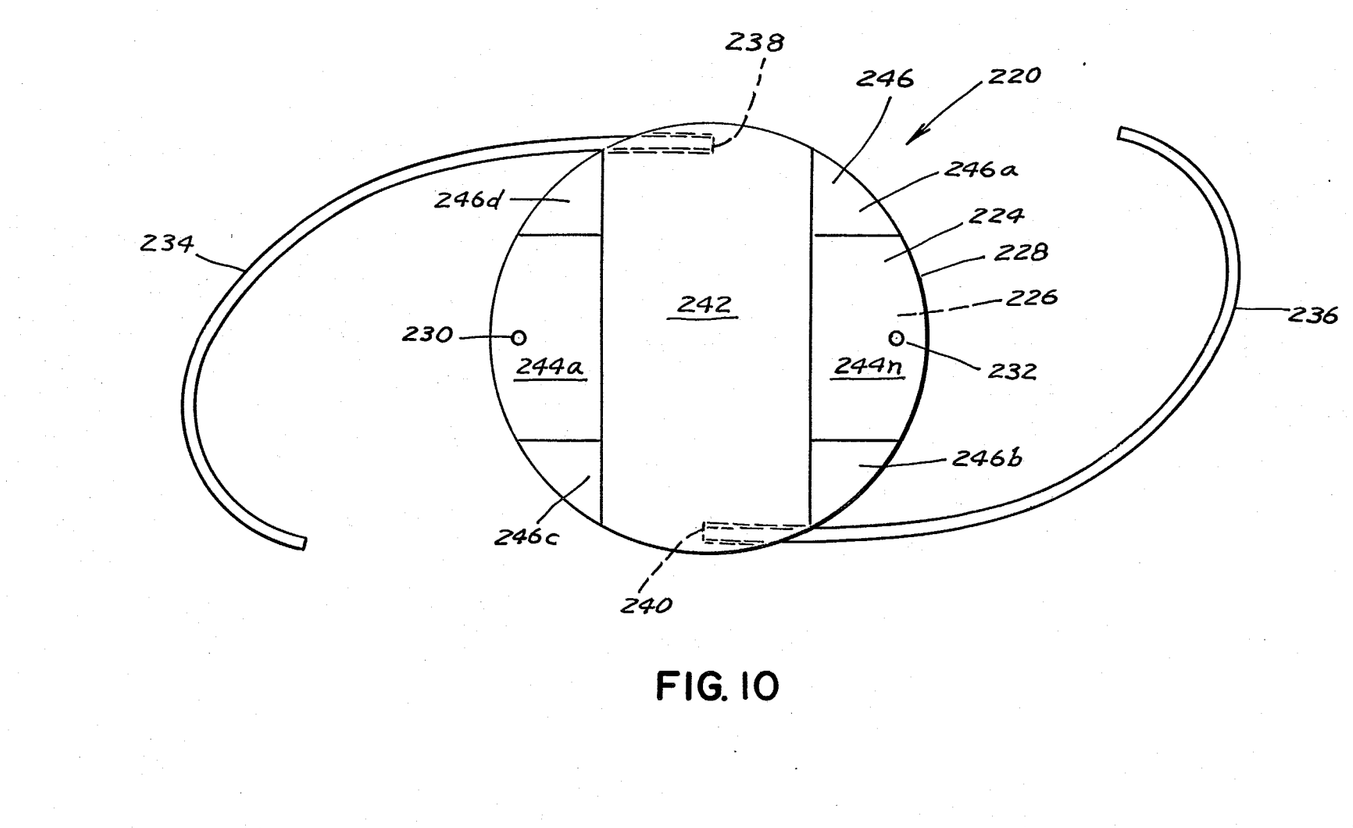
FIG. 10 illustrates a plan view of an embodiment of the multiple element zone of focus lens having both horizontal and vertical divisions between the lens elements with the vertical element dominating.

FIG. 10 illustrates an arrangement comparable to that of FIG. 9, but with the central lens element arranged in the vertical plane. The lens 220 includes an optic 222, a convex anterior surface 224, a planto surface 226, an edge 228 therebetween, and positioning holes 230 and 232 and haptic 234 and 236 engaged in holes 238 and 240. The optic 222 includes a vertically aligned lens element 242, horizontally aligned lens elements 244a–244n perpendicular to the vertically aligned lens element 242 in a lens body 246 including portions 246a–246d. This geometrical configuration may employ combinations of differing powers and colors as previously described.

Figure 11:
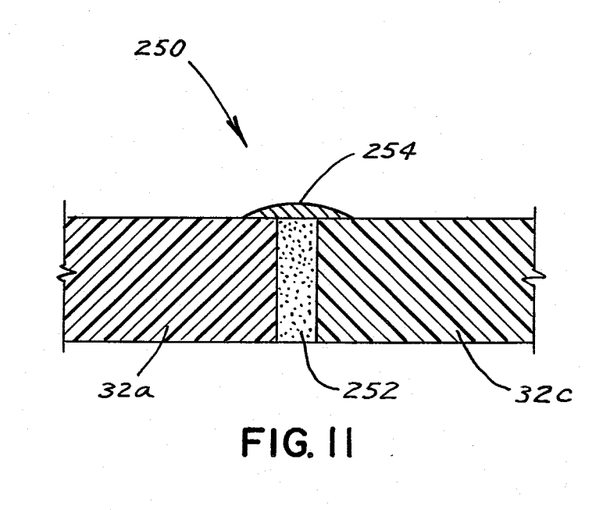
FIG. 11 illustrates a sectional view taken across a junction between the lens elements to show the anti-reflective coating and masking material; and, FIG. 12 illustrates a plan view of paired lenses for use in the left and right eyes of a patient.

FIG. 11 illustrates a cross-sectional view at the junction 250 between elements joined with adhesive or other suitable material taken along line 11—11 of FIG. 1. A lens element 32a is joined to a lens element 32c with a suitable adhesive material 254. An opaque layer 256 of highly pigmented material may be added to reduce reflection caused by the junction between the elements. The adhesive material 254 may contain an anti-reflection material or such material may be applied directly to the abutting surfaces.

Figure 12:
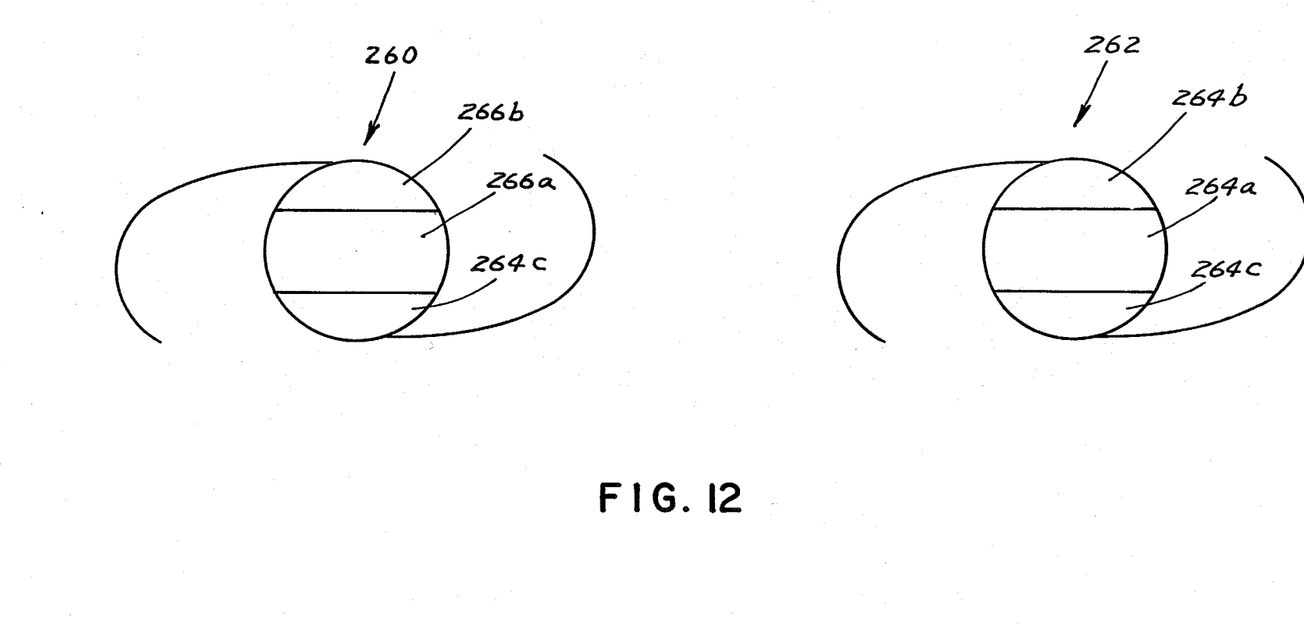

FIG. 12 illustrates two lenses 260 and 262 for the right and left eye, respectively, having lens elements of comparable power and color arranged in the same geometric position in each lens. For example, lens element 264a for the left eye, has the same power and color as the lens element 266a for the right eye. In this embodiment, the lens elements 264a–264c for the left eye have powers respectively corresponding to the powers of lens elements 266a–266c for the right eye. This too, is to facilitate the adaptation process.

MODE OF OPERATION

Reduction of the cost of the lenses would have the effect of increasing the availability of this procedure to those who currently lack the economic means to afford such an operation. This is particularly the case in third world countries where costs are often the overriding consideration in medical care.

There is no question that the technique of using less than the entire retina is usually not as desirable as a system which duplicates the normal lens use of the entire retina. There is a loss of acuity which shows up in reduced resolution and contrast, particularly in low light conditions. In addition, the accommodation of the brain to such a system takes a period of time, and the degree of success in such accommodation varies with individuals. There are, of course, minor problems when taken in view of the alternative, which is blindness.

In the case where a defective natural lens is to be replaced, it is customary to make extensive measurements on the eye prior to the removal of the defective natural lens and its replacement with a fixed focus implantable lens. Such measurements allow the selection of a lens having appropriate power for the individual, and the nominal distance to the object which is desired to be brought into focus on the retina. This approach to the problem has the disadvantage that a wide range of powers must be available to the surgeon. Since each lens is individually fabricated, the economic burden of fabricating a wide variety of powers adds substantially to the cost of lenses. It would be much cheaper to manufacture only a few lenses and use them in all patients. The cost of manufacture would be reduced and inventory requirements would be much less burdensome.

Various modifications can be made to the present invention without departing from the apparent scope thereof.

I claim:

1. A zone of focus lens for use with an eye comprising:
   a. a plurality of lens elements joined to form a unitary lens structure having a front surface, a rear surface and a circular periphery;
   b. each of said lens elements serving to create an image on a distinct portion of the retina;
   c. at least two of said lens elements having different powers whereby objects at different distances from the eye are simultaneously brought to a focus on distinct portions of the retina; and,
   d. at least two of said lens elements are different colors.

2. A lens according to claim 1 wherein said lens elements are round.

3. A lens according to claim 2 wherein at least two of said lens elements are of materials having different indices of refraction.

4. A lens according to claim 1 comprised of lens elements each having different indices of refraction.

5. A lens according to claim 4 consisting of three lens elements.

6. A lens according to claim 5 having a horizontally oriented lens element larger than said other lens elements.

7. A lens according to claim 5 having a vertically oriented lens element larger than said other lens elements.

8. A lens according to claim 5 wherein said lens elements are horizontally oriented.

9. A lens according to claim 5 wherein said lens elements are vertically oriented.

10. A lens according to claim 3 wherein the junctions between lens elements includes an anti-reflective coating.

11. First and second lenses according to claim 1 for use in left and right eyes wherein like power elements are similarly positioned.

* * * * *